US008071608B2

(12) United States Patent
Bennett et al.

(10) Patent No.: US 8,071,608 B2
(45) Date of Patent: Dec. 6, 2011

(54) THERAPEUTIC AGENTS

(75) Inventors: Stuart Norman Lile Bennett, Macclesfield (GB); Rolf Peter Walker, Macclesfield (GB); Michael James Waring, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/756,436

(22) Filed: Apr. 8, 2010

(65) Prior Publication Data
US 2010/0261733 A1 Oct. 14, 2010

Related U.S. Application Data

(60) Provisional application No. 61/168,048, filed on Apr. 9, 2009.

(51) Int. Cl.
*A01N 43/90* (2006.01)
*A61K 31/519* (2006.01)
*C07D 487/00* (2006.01)

(52) U.S. Cl. .................... 514/262.1; 544/262
(58) Field of Classification Search .......... None
See application file for complete search history.

(56) References Cited

U.S. PATENT DOCUMENTS

| 2,750,393 | A | 6/1956 | Elpern |
| 2,967,194 | A | 1/1961 | Hauptschein |
| 3,917,625 | A | 11/1975 | Lee et al. |
| 3,950,351 | A | 4/1976 | Rossignol et al. |
| 4,009,174 | A | 2/1977 | Cluzan et al. |
| 4,105,785 | A | 8/1978 | Mauvernay et al. |
| 4,146,631 | A | 3/1979 | Ford et al. |
| 4,434,170 | A | 2/1984 | Dostert et al. |
| 4,474,792 | A | 10/1984 | Erickson |
| 4,634,783 | A | 1/1987 | Fujii et al. |
| 4,966,891 | A | 10/1990 | Fujiu et al. |
| 5,258,407 | A | 11/1993 | Washburn et al. |
| 5,273,986 | A | 12/1993 | Holland et al. |
| 5,399,702 | A | 3/1995 | Holland et al. |
| 5,466,715 | A | 11/1995 | Washburn et al. |
| 5,510,478 | A | 4/1996 | Sabb |
| 5,661,153 | A | 8/1997 | Isobe et al. |
| 5,672,750 | A | 9/1997 | Perry |
| 5,712,270 | A | 1/1998 | Sabb |
| 5,849,735 | A | 12/1998 | Albright et al. |
| 5,939,462 | A | 8/1999 | Connell et al. |
| 6,110,945 | A | 8/2000 | Head et al. |
| 6,197,798 | B1 | 3/2001 | Fink et al. |
| 6,200,995 | B1 | 3/2001 | De la Brouse-Elwood et al. |
| 6,207,693 | B1 | 3/2001 | Setoi et al. |
| 6,214,878 | B1 | 4/2001 | Bernardon et al. |
| 6,242,474 | B1 | 6/2001 | Yamasaki et al. |
| 6,245,817 | B1 | 6/2001 | Connell et al. |
| 6,255,335 | B1 | 7/2001 | Himmler et al. |
| 6,316,482 | B1 | 11/2001 | Setoi et al. |
| 6,320,050 | B1 | 11/2001 | Bizzarro et al. |
| 6,348,474 | B1 | 2/2002 | Kayakiri et al. |
| 6,369,229 | B1 | 4/2002 | Head et al. |
| 6,376,515 | B2 | 4/2002 | Zhu et al. |
| 6,388,071 | B2 | 5/2002 | Mahaney |
| 6,448,399 | B1 | 9/2002 | Corbett et al. |
| 6,486,349 | B1 | 11/2002 | Flitter et al. |
| 6,528,543 | B1 | 3/2003 | Bizzarro et al. |
| 6,545,155 | B2 | 4/2003 | Corbett et al. |
| 6,610,846 | B1 | 8/2003 | Bizzarro et al. |
| 6,613,942 | B1 | 9/2003 | Ling et al. |
| 7,132,546 | B2 | 11/2006 | Kato et al. |
| 7,199,140 | B2 | 4/2007 | Hayter et al. |
| 7,230,108 | B2 | 6/2007 | Hargreaves et al. |
| 7,390,908 | B2 | 6/2008 | Boyd et al. |
| 7,524,957 | B2 | 4/2009 | Boyd et al. |
| 7,642,259 | B2 | 1/2010 | McKerrecher et al. |
| 7,642,263 | B2 | 1/2010 | McKerrecher et al. |
| 7,671,060 | B2 | 3/2010 | Martin et al. |
| 7,696,191 | B2 | 4/2010 | McCabe et al. |
| 7,700,640 | B2 | 4/2010 | Cornwall et al. |
| 7,745,475 | B2 | 6/2010 | Johnstone et al. |
| 7,842,694 | B2 | 11/2010 | McKerrecher et al. |
| 2001/0027200 | A1 | 10/2001 | De la Brouse-Elwood et al. |
| 2002/0002183 | A1 | 1/2002 | Zhu et al. |
| 2002/0095044 | A1 | 7/2002 | Jagtap et al. |
| 2003/0162690 | A1 | 8/2003 | Zhu et al. |
| 2003/0228982 | A1 | 12/2003 | Helmke et al. |
| 2004/0014968 | A1 | 1/2004 | Bizzarro et al. |
| 2004/0077555 | A1 | 4/2004 | Ishihara et al. |
| 2004/0214868 | A1 | 10/2004 | Hayter et al. |

(Continued)

FOREIGN PATENT DOCUMENTS

CA 2605738 * 11/2006

(Continued)

OTHER PUBLICATIONS

Alvarez et al. "Evidence that glucokinase regulatory protein is expressed and interacts with glucokinase in rat brain" J. Neurochem. 80(1):45-53 (2002). Alvarez et al. "Expression of the glucagon-like peptide-1 receptor gene in rat brain" J. Neurochem. 66(3):920-927 (1996).
Anderson et al "Pyridopyrimidines. 6. Nucleophilic substitutions in the pyrido[2,3-d]pyrimidine series" J. Org. Chem. 42(6):993-996 (1977).
Ando et al. "Fluoride salts on alumina as reagents for alkylation of phenols and alcohols" Bull. Chem. Soc. Jpn. 55(8):2504-2507 (1982).
Atwell et al. "Potential antitumor agents. VI. Bisquaternary salts" J. Med. Chem. 11(2):295-300 (1968).
Baker et al. "Structure and synthesis of Pallescansin E utilising a modified Wadsworth-Emmons reaction" J. Chem. Soc., Perkin Trans. 1, 12:3087-3091 (1981).
Baker et al. "Synthesis of Pallescensin-E: Use of crown ether in the Wadsworth procedure for olefin formation" Tetrahedron Letters 22:161-162 (1981).

(Continued)

Primary Examiner — Jeffrey Murray
(74) Attorney, Agent, or Firm — Morgan, Lewis & Bockius LLP

(57) ABSTRACT (2S)-2-[1-(2-Chloro-6-cyano-phenyl)pyrazolo[4,5-e]pyrimidin-4-yl]oxy-3-[(1R)-2-hydroxy-1-methyl-ethoxy]-N-(5-methylpyrazin-2-yl)propanamide or a pharmaceutically acceptable salt thereof is useful in the treatment or prevention of a disease or medical condition mediated through glucokinase (GLK or GK), leading to a decreased glucose threshold for insulin secretion.

5 Claims, No Drawings

U.S. PATENT DOCUMENTS

| | | | |
|---|---|---|---|
| 2005/0080106 A1 | 4/2005 | Boyd et al. | |
| 2005/0148605 A1 | 7/2005 | Grotzfeld et al. | |
| 2005/0165074 A1 | 7/2005 | Grotzfeld et al. | |
| 2005/0171171 A1* | 8/2005 | Mehta et al. | |
| 2005/0171172 A1* | 8/2005 | Lai et al. | |
| 2005/0261315 A1* | 11/2005 | Mehta et al. | |
| 2006/0004010 A1* | 1/2006 | Habashita et al. | |
| 2006/0058353 A1* | 3/2006 | Mckerrecher et al. | |
| 2006/0167053 A1* | 7/2006 | Iino et al. | |
| 2006/0178399 A1* | 8/2006 | Nishizawa et al. | |
| 2006/0258728 A1* | 11/2006 | Tani et al. | |
| 2007/0078168 A1* | 4/2007 | Caulkett | |
| 2007/0093535 A1* | 4/2007 | Hayter et al. | |
| 2007/0112040 A1* | 5/2007 | Hayter et al. | |
| 2007/0255062 A1* | 11/2007 | Johnstone et al. | |
| 2007/0287693 A1* | 12/2007 | Johnstone et al. | |
| 2008/0015203 A1* | 1/2008 | Johnstone et al. | |
| 2008/0057074 A1 | 3/2008 | Takaoka et al. | |
| 2008/0153800 A1* | 6/2008 | McCabe et al. | |
| 2008/0171734 A1* | 7/2008 | Campbell et al. | |
| 2008/0200694 A1* | 8/2008 | Cornwall et al. | |
| 2008/0234273 A1* | 9/2008 | McKerrecher et al. | |
| 2008/0280872 A1* | 11/2008 | Johnstone et al. | |
| 2008/0280874 A1* | 11/2008 | Johnstone et al. | |
| 2008/0300412 A1* | 12/2008 | Hopes et al. | |
| 2008/0312207 A1* | 12/2008 | Johnstone et al. | |
| 2008/0318968 A1* | 12/2008 | Martin et al. | |
| 2009/0018157 A1* | 1/2009 | Johnstone et al. | |
| 2009/0029905 A1* | 1/2009 | McKerrecher et al. | |
| 2009/0062351 A1* | 3/2009 | Caulkett et al. | |
| 2009/0105214 A1* | 4/2009 | McKerrecher et al. | |
| 2009/0105263 A1* | 4/2009 | Caulkett et al. | |
| 2009/0111790 A1* | 4/2009 | McKerrecher et al. | |
| 2009/0118159 A1* | 5/2009 | McKerrecher et al. | |
| 2009/0131403 A1* | 5/2009 | Kusuda et al. | |
| 2009/0227592 A1* | 9/2009 | Boyd et al. | |
| 2009/0253676 A1* | 10/2009 | Johnstone et al. | |
| 2009/0264336 A1* | 10/2009 | McKerrecher et al. | |
| 2010/0094009 A1* | 4/2010 | McCabe et al. | |
| 2010/0210621 A1* | 8/2010 | Bowden et al. | |
| 2010/0210841 A1* | 8/2010 | Butters et al. | |

FOREIGN PATENT DOCUMENTS

| | | | |
|---|---|---|---|
| CS | 173097 | * | 6/1978 |
| EP | 0316704 | * | 5/1989 |
| EP | 0353452 | * | 2/1990 |
| EP | 0219436 | * | 12/1993 |
| EP | 0619116 | * | 10/1994 |
| EP | 0841339 | | 5/1998 |
| EP | 1048659 | * | 11/2000 |
| EP | 1132381 | * | 9/2001 |
| EP | 0620216 | * | 1/2003 |
| EP | 1336607 | * | 8/2003 |
| EP | 1357116 | * | 10/2003 |
| EP | 1400540 | * | 3/2004 |
| EP | 1496052 | * | 1/2005 |
| EP | 1790637 | * | 5/2005 |
| EP | 1541563 | * | 6/2005 |
| EP | 1532980 | * | 11/2005 |
| EP | 1600442 | * | 11/2005 |
| EP | 1604981 | * | 12/2005 |
| EP | 1702919 | * | 9/2006 |
| EP | 1995246 | * | 11/2008 |
| FR | 1526074 | * | 5/1968 |
| FR | 2088019 | * | 1/1972 |
| GB | 1352415 | * | 5/1974 |
| GB | 1561350 | * | 2/1980 |
| GB | 1588242 | * | 4/1981 |
| GB | 2216517 | * | 10/1989 |
| GB | 2331748 | | 6/1999 |
| GB | 2385328 | | 8/2003 |
| JP | 50105559 | | 8/1975 |
| JP | 57021320 | | 2/1982 |
| JP | 57075962 | | 5/1982 |
| JP | 58069812 | | 4/1983 |
| JP | 61205937 | | 9/1986 |
| JP | 62158252 | | 7/1987 |
| JP | 04300832 | | 10/1992 |
| JP | 04300874 | | 10/1992 |
| JP | 06027025 | | 2/1994 |
| JP | 08143565 | | 6/1996 |
| JP | 08173525 | | 7/1996 |
| JP | 08301760 | | 11/1996 |
| JP | 09040557 | | 2/1997 |
| JP | 09202786 | | 8/1997 |
| JP | 10101671 | | 4/1998 |
| JP | 10101672 | | 4/1998 |
| JP | 10212271 | | 8/1998 |
| JP | 11029480 | | 2/1999 |
| JP | 11171848 | | 6/1999 |
| JP | 11222435 | | 8/1999 |
| JP | 11292879 | | 10/1999 |
| JP | 2000086657 | | 3/2000 |
| WO | WO 91/09017 | | 6/1991 |
| WO | WO 94/04525 | | 3/1994 |
| WO | WO 94/12461 | | 6/1994 |
| WO | WO 95/20578 | | 8/1995 |
| WO | WO 95/35298 | | 12/1995 |
| WO | WO 96/11902 | | 4/1996 |
| WO | WO 96/19455 | | 6/1996 |
| WO | WO 96/22282 | | 7/1996 |
| WO | WO 96/22293 | | 7/1996 |
| WO | WO 96/22294 | | 7/1996 |
| WO | WO 96/22295 | | 7/1996 |
| WO | WO 96/36619 | | 11/1996 |
| WO | WO 96/41795 | | 12/1996 |
| WO | WO 97/24355 | | 7/1997 |
| WO | WO 97/36480 | | 10/1997 |
| WO | WO 97/46560 | | 12/1997 |
| WO | WO 97/49707 | | 12/1997 |
| WO | WO 97/49708 | | 12/1997 |
| WO | WO 98/24771 | | 6/1998 |
| WO | WO 98/34632 | | 8/1998 |
| WO | WO 98/35944 | | 8/1998 |
| WO | WO 98/45242 | | 10/1998 |
| WO | WO 99/00359 | | 1/1999 |
| WO | WO 99/00372 | | 1/1999 |
| WO | WO 99/17777 | | 4/1999 |
| WO | WO 99/20611 | | 4/1999 |
| WO | WO 99/24415 | | 5/1999 |
| WO | WO 99/26944 | | 6/1999 |
| WO | WO 99/32477 | | 7/1999 |
| WO | WO 99/38845 | | 8/1999 |
| WO | WO 99/54301 | | 10/1999 |
| WO | WO 99/62901 | | 12/1999 |
| WO | WO 00/02850 | | 1/2000 |
| WO | WO 00/26202 | | 5/2000 |
| WO | WO 00/39118 | | 7/2000 |
| WO | WO 00/46203 | | 8/2000 |
| WO | WO 00/58293 | | 10/2000 |
| WO | WO 01/00579 | | 1/2001 |
| WO | WO 01/12621 | | 2/2001 |
| WO | WO 01/16097 | | 3/2001 |
| WO | WO 01/19788 | | 3/2001 |
| WO | WO 01/20327 | | 3/2001 |
| WO | WO 01/26652 | | 4/2001 |
| WO | WO 01/32639 | | 5/2001 |
| WO | WO 01/44216 | | 6/2001 |
| WO | WO 01/64642 | | 9/2001 |
| WO | WO 01/64643 | | 9/2001 |
| WO | WO 01/74791 | | 10/2001 |
| WO | WO 01/83465 | | 11/2001 |
| WO | WO 01/83478 | | 11/2001 |
| WO | WO 01/85706 | | 11/2001 |
| WO | WO 01/85707 | | 11/2001 |
| WO | WO 02/00633 | | 1/2002 |
| WO | WO 02/08209 | | 1/2002 |
| WO | WO 02/14312 | | 2/2002 |
| WO | WO 02/24682 | | 3/2002 |
| WO | WO 02/26718 | | 4/2002 |
| WO | WO 02/26731 | | 4/2002 |
| WO | WO 02/28835 | | 4/2002 |
| WO | WO 02/42270 | | 5/2002 |
| WO | WO 02/46173 | | 6/2002 |
| WO | WO 02/48106 | | 6/2002 |
| WO | WO 02/051831 | | 7/2002 |

| | | |
|---|---|---|
| WO | WO 02/064545 | 8/2002 |
| WO | WO 02/079145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |
| WO | WO 2004/007472 | 1/2004 |
| WO | WO 2004/009602 | 1/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/080966 | 9/2004 |
| WO | WO 2004/081001 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/042513 | 5/2005 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/030925 | 3/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/030567 | 3/2007 |
| WO | WO 2007/031739 | 3/2007 |
| WO | WO 2007/053657 | 5/2007 |
| WO | WO 2007/060448 | 5/2007 |
| WO | WO 2007/075847 | 7/2007 |
| WO | WO 2007/105637 | 9/2007 |
| WO | WO 2007/143434 | 12/2007 |
| WO | WO 2008/050101 | 5/2008 |
| WO | WO 2008/050117 | 5/2008 |
| WO | WO 2008/075073 | 6/2008 |
| WO | WO 2008/148832 | 12/2008 |
| WO | WO 2010/015849 | 2/2010 |

OTHER PUBLICATIONS

Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).
Beilstein Registry No. 6511458 (Apr. 18, 1994) [XP002272206].
Bell et al. "Glucokinase mutations, insulin secretion, and diabetes mellitus" Annu. Rev. Physiol. 58:171-186 (1996).
Beller et al. "Photochemical synthesis of benzo[f]quinolines" J Org Chem. 42(22):3514-3518 (1977).
Berl et al. "Induced fit selection of a barbiturate receptor from a dynamic structural and conformational/ configurational library" European J. Org. Chem. (11):3089-3094 (1999).
Berl et al. "Template-induced and molecular recognition directed hierarchical generation of supramolecular assemblies from molecular strands" Chem. Eur. J. 6(11):1938-1946 (2000).
Bonina et al. "Synthesis and pharmacologic activity of 2-arylethenylthiazol-4-acetic and 4-carboxylic acids" Il Farmaco 40(11):875-884 (1985).
Boucherle et al. "Recherches dans la serie des cetones polyphenoliques IV. Thiazoles" Chimica Therapeutica. 3(5):360-363 (1968) (Translation enclosed).
Bowden et al. "Structure-activity relations. Part 10. Metal-ion-complexation studies of a series of substituted benzamidotetrazoles" J. Chem. Research (Synopses) 11:304 (1991).
Bowden et al. "Structure-activity relations. Part 13 Inhibitors of cyclic nucleotide phosphodiesterase and anaphylaxis. Inhibition by a series of substituted benzamidotetrazoles" J. Chem. Research (Synopses) 6:206 (1992).
Brenner et al. "Imino-bridged heterocycles. VII. (1) N-aminobenzocycloheptapyridinimines" J. Heterocyclic Chem. 23:1331-1332 (1986).
Brocklehurst et al. "Stimulation of hepatocyte glucose metabolism by novel small molecule glucokinase activators" Diabetes 53:535-541 (2004).
Caira "Crystalline polymorphism of organic compounds" Topics in Current Chemistry 198:163-208 (1998).
Caro et al. "Liver glucokinase: Decreased activity in patients with type II diabetes" Horm. Metab. Res. 27(1):19-22 (1995).
Carroll et al. "The in vitro characterisation of a novel Glucokinase activator" Stress, Signalling and Control, Biochemical Society Meeting 679, University of Essex, UK (Jul. 2-4, 2003).
Caulfield et al. "The first potent and selective inhibitors of the glycine transporter type 2" J. Med. Chem. 44(17):2679-2682 (2001).
Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978) (Translation enclosed).
Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].
Chemical Abstracts Service, Columbus, Ohio, US: CAS Registry No. 354767-51-4 (Sep. 5, 2001).
Chemical Abstracts Service, Columbus, Ohio, US: CAS Registry No. 354767-66-1 (Sep. 5, 2001).

Chemical Abstracts Service, Columbus, Ohio, US: CAS Registry No. 438028-05-8 (Nov. 15, 2001); CAS Registry No. 438024-90-9 (Nov. 15, 2001), [XP002272448].

Christesen et al. "The second activating glucokinase mutation (A456V): Implications for glucose homeostasis and diabetes therapy" Diabetes 51(4):1240-1246 (2002).

Ciaceri et al. "Analgesic, antipyretic and anti-inflammatory action of some new acids of the phenylethylenethiazole series" Minerva Medica 63(42):2409-2413 (1972).

Coburn et al. "Mesoionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7- diones" J. Pharm. Sciences. 62(11):1785-1789 (1973).

Coghlan "Small molecule Glucokinase Activators (GKAs) as novel anti-diabetic agents" CIDEM seminar (May 2005).

Coghlan "Small molecule Glucokinase Activators (GKAs) as novel anti-diabetic agents" Society for Medicines Research Seminar (Jun. 2004).

Coghlan et al. "Glucokinase activators in diabetes management" Expert Opin. Investig. Drugs 17(2):145-167 (2008).

Coope et al. "Predictive blood glucose lowering efficacy by Glucokinase activators in high fat fed female Zucker rats" British Journal of Pharmacology 149(3):328-335 (2006).

Corbett "Glucokinase activators: Discovery of novel, orally active glucose lowering agents" Abstract, Cambridge Healthtech Institute's Eleventh Annual Molecular Medicine Tri-Conference, Moscone West Convention Center, San Francisco, CA (Mar. 24-26, 2004).

Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Francisco, CA (Mar. 24-26, 2004).

Cushman et al. "Synthesis and evaluation of new protein-tyrosine kinase inhibitors. Part 1. Pyridine-containing stilbenes and amides" Bioorganic & Medicinal Chemistry Letters 1(4):211-214 (1991).

De Paulis et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem. 25:507-517 (1990).

DeFronzo et al. "The triumvirate: β-cell, muscle, liver. A collusion responsible for NIDDM" Diabetes 37:667-687 (1988).

DeJohn et al. "Functionalization of Substituted 2(1H)- and 4(1H)-Pyridones. III. The preparation of substituted 6-vinyl-1,2-dihydro-2-oxo—and 1,4-dihydro-4-oxo-3-pyridinecarboxylic acids through the chemistry of pyridone dianions" J. Heterocyclic Chem. 20(5):1295-1302 (1983).

Desai et al. "Phenotypic correction of diabetic mice by adenovirus-mediated glucokinase expression" Diabetes 50:2287-2295 (2001).

Edmont et al. "Synthesis and evaluation of quinoline carboxyguanidines as antidiabetic agents" Bioorg. Med. Chem. Lett. 10(16):1831-1834 (2000).

Elpern et al. "Iodinated Benzamidotetrazoles" J. Org. Chem. 22:1686 (1957).

Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.

Ferre et al. "Correction of diabetic alterations by glucokinase" PNAS USA 93(14):7225-7230 (1996).

Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem. 29(4):538-549 (1986).

Froguel et al. "Familial hyperglycemia due to mutations in glucokinase—Definition of a subtype of diabetes mellitus" New Engl. J. Med. 328:697-702 (1993).

Fujimoto et al. "Administration of D-glucosamine into the third cerebroventricle induced feeding accompanied by hyperglycemia in rats" Life Sciences 37(26):2475-2482 (1985).

Gill et al. "Stimulation of Insulin Release by a small molecule glucokinase activator" EASD Islet Study Group, Abstract (Nov. 2005).

Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Glaser et al. "Familial hyperinsulinism caused by an activating glucokinase mutation" The New England Journal of Medicine 338(4):226-230 (1998).

Gorman et al. "Effect of high-fat diet on glucose homeostasis and gene expression in Glucokinase (GK) heterozygous knock-outs" Abstract Number: 0108-OR, 67th Annual Scientific Sessions, American Diabetes Association, Chicago, IL (Jun. 22-26, 2007).

Grimsby "Glucokinase activators: Potential treatment for type 2 diabetes" Roche, SMi Diabetes, London, UK (Oct. 28-29, 2002).

Grimsby et al. "Allosteric activators of glucokinase: Potential role in diabetes therapy" Science 301(5631):370-373 (2003).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding and proton transfer interactions" Israel Journal of Chemistry 32:105-111 (1992).

Horsak et al. "Method of evaluation of the phase diagram of a system with formation of a compound" Chem. Zvesti. 36(3):311-320 (1982).

Ismail et al., "Synthesis of Some New Biologically Active Sulfur Compounds Containing Pyrazolo[3,4-d]pyrimidine Moiety" Phosphorus, Sulfur and Silicon and the Related Elements 178:1795-1805 (2003).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50—A glucokinase activator" Abstract No. 0592-P, 67th Annual Scientific Sessions, American Diabetes Association, Chicago, IL (Jun. 22-26, 2007).

Julia et al. "Synthesis of a 2,3,4,4a,5,6-hexahydrobenzo[f]quinoline system by "aryne substitution"" Bull Chem Soc France 11:4463-4467 (1968) (Translation enclosed).

Kamata et al. "Pyroelectricity of noncentrosymmetric Langmuir-Blodgett films of phenylpyrazine derivatives" Japan J. Appl. Phys. 33(2):1074-1078 (1994).

Kar "Cinchophen analogues as potential CNS agents" J Pharm Sci. 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to a threefold pyridine arylamide receptor. Enhancement of the stability of supramolecular solution structures by multiple binding sites" J. Org. Chem. 60(13):4291-4293 (1995).

Kunishima et al. "4-(4,6-Dimethoxy-1,3,5-triazin-2-yl)-4-methylmorpholinium chloride: An efficient condensing agent leading to the formation of amides and esters" Tetrahedron 55:13159-13170 (1999).

Kurata et al. "D-Glucose suppression of eating after intra-third ventricle infusion in rat" Physiology & Behavior 37:615-620 (1986).

Kurata et al. "Structural evaluation of glucose analogues on feeding elicitation in rat" Metabolism 38(1):46-51 (1989).

Lai et al. "Formation of columnar arrangements in copper(ii) complexes of 2-phenylazomethinopyridine derivatives" J. Materials Chemistry 8(11):2379-2383 (1998).

Leighton et al. "Improved glycemic control after sub-acute administration of a Glucokinase activator to male zucker (fa/fa) rats" Abstract No. 0377-OR, 67th Annual Scientific Sessions, American Diabetes Association, Chicago, IL (Jun. 22-26, 2007).

Leighton et al. "Small molecule glucokinase activators as novel anti-diabetic agents" Biochemical Society Transactions 33(Part 2):371-374 (2005).

Leighton, "Pre-clinical disease models—challenges and success stories" 44th Drug Information Association Annual Meeting, Boston, MA, US (2008).

Levin "Glucosensing neurons do more than just sense glucose" International Journal of Obesity 25(Suppl 5): S68-S72 (2001).

Levin et al. "Brain glucose sensing and body energy homeostasis: role in obesity and diabetes" Am. J. Physiol. 276(5 Pt 2):R1223-R1231 (1999).

Levin et al. "Differential effects of diet and obesity on high and low affinity sulfonylurea binding sites in the rat brain" Brain Research 739(1-2):293-300 (1996).

Levin et al. "In vivo and in vitro regulation of [3H]glyburide binding to brain sulfonylurea receptors in obesity-prone and resistant rats by glucose" Brain Research 776(1-2):146-153 (1997).

Levin et al. "Reduced glucose-induced neuronal activation in the hypothalamus of diet-induced obese rats" Brain Research 808(2):317-319 (1998).

Levkoev et al. "Research on cyanide dyes 11. 7,7'-Dimethylthiacarbocyanines" Zhurnal Obshchei Khimii 27:3097-3107 (1957) (Translation enclosed).

Lith, "Evaluation of the effects on whole body glucose metabolism after single doses of X2000—A glucose lowering agent" Poster presentation, Master thesis in Pharmaceutical Bioscience, Goteborgs University (2008).

Lynch et al. "Localization of glucokinase gene expression in the rat brain" Diabetes 49(5):693-700 (2000).

Mastafanova et al. "Features of the catalytic reduction of 4-(3-oxoquinuclidyl-2-methylene)-6-methoxyquinoline and its ethyleneketal" Khimiya Geterotsiklicheskikh Soedinenii (1):86-94 (1989) (Translation enclosed).

Mastafanova et al. "Synthesis and study of the antihypertensive activity of substituted N-acetylmercaptopropionyl-6-[2'-phenylethyl]pipecolinic acids" Khimiko Farmatsevticheskii Zhurnal 22(3):294-302 (1988).

Mastafanova et al. "Synthesis, Anti-Inflammatory and Analgesic Activity of 1,6-Disubstituted Pipecolic and 6-Substituted Picolinic Acids" Khimiko Farmatsevticheskii Zhurnal 22(4) 428-431 (1988).

Mazik et al. "Molecular recognition of carbohydrates by artificial polypyridine and polypyrimidine receptors" Angewandte Chemie International Edition 39(3):551-554 (2000).

Mazik et al. "Molecular recognition of carbohydrates by artificial receptors: systematic studies towards recognition motifs for carbohydrates" Chem. Eur. J. 7(3):664-670 (2001).

McKerrecher "Design and synthesis of novel glucokinase activators" 13th RSC-SCI Medicinal Chemistry Symposium, Churchill College, Cambridge (Sep. 4-7, 2005).

McKerrecher et al. "Design & synthesis of novel glucokinase activators as potential treatments for type 2 diabetes" 233rd ACS National Meeting, Chicago, IL (Mar. 25-29, 2007).

McKerrecher et al. "Design and synthesis of novel glucokinase activators as potential treatment for type 2 diabetes" Frontiers in Medicinal Chemistry, Frankfurt (Mar. 12-15, 2006).

McKerrecher et al. "Design of a potent, soluble glucokinase activator with excellent in vivo efficacy" Bioorg. Med. Chem. Left. 16(10):2705-2709 (May 15, 2006) Epub Feb. 28, 2006.

McKerrecher et al. "Discovery, synthesis and biological evaluation of novel glucokinase activators" Bioorg Med Chem Lett. 15(8):2103-2106 (2005).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr. 1, 2004 (paper 341).

McKerrecher et al. "Identification of orally bioavailable small molecule activators of glucokinase" Abstract, Anglo-Swedish Medicinal Chemistry Meeting (Mar. 2005).

Meijer et al "Chiral amplification in supramolecular stacks" Polymer Preprints 41(1):902-903 (2000).

Mobbs et al. "Brain glucose-sensing mechanisms: ubiquitous silencing by aglycemia vs. hypothalamic neuroendocrine responses" Am. J. Physiol. Endocrinol. Metab. 281(4):E649-E654 (2001).

Moore et al. "Acute fructose administration improves oral glucose tolerance in adults with type 2 diabetes" Diabetes Care 24(11):1882-1887 (2001).

Motesharei et al. "Molecular recognition in membrane mimics: a fluorescence probe" J. Am. Chem. Soc. 116(16):7413-7414 (1994).

Motesharei et al. "Molecular recognition on functionalized self-assembled monolayers of alkanethiols on gold" J. Am. Chem. Soc. 120(29): 7328-7336 (1998).

Palmans "Extended-core discotic liquid crystals based on the intramolecular H-bonding in N-acylated 2,2'-bipyridine-3,3'-diamine moieties" Chem. Eur. J. 3(2):300-307 (1997).

Plieninger et al. "Synthesis of 7,8-dihydro-5,6-benzoquinoline-(3)-carboxylic acid" Chemische Berichte 87:882-887 (1954) (Translation enclosed).

Printz et al. "Mammalian glucokinase" Annu. Rev. Nutr. 13:463-496 (1993).

Prousek et al. "Preparation and electron transfer-induced cis-trans isomerization reactions of 1-(5-nitro-2-furyl)-, 1-(5-nitro-2-thienyl)-, and 1-(4-nitrophenyl)-2-R ethylenes" Collect. Czech. Chem. Commun. 54:1675-1682 (1989).

Qian-Cutrone et al. "Glucolipsin A and B, two new glucokinase activators produced by *Streptomyces purpurogeniscleroticus* and *Nocardia vaccinii*" Journal of Antibiotics (Tokyo), 52(3):245-255 (1999).

Ralph et al. "Glucose Modulation of Glucokinase Activation by Small Molecules" Biochemistry 47(17):5028-5036 (2008).

Ready et al., "Asymmetric Catalytic Synthesis of α-Aryloxy Alcohols: Kinetic Resolution of Terminal Epoxides via Highly Enantioselective Ring Opening with Phenols" J. Am. Chem. Soc. 121:6086-6087 (1999).

Rivalle et al. "2,3 Disubstituted furans and pyrroles—XVIII: Synthesis and rearrangement of 4H-dihydro-9,10 benzo[4,5]cyclohepta[1,2-b]furannones-4" Tetrahedron 32(7):829-834 (1976).

Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).

Rogers et al. "Mesoionic purinone analogues as inhibitors of cyclic-AMP phosphodiesterase: a comparison of several ring systems" J. Med. Chem. 24(11):1284-1287 (1981).

Roncero et al. "Functional glucokinase isoforms are expressed in rat brain" J. Neurochem. 74(5):1848-1857 (2000).

Rowe et al. "Potassium channel dysfunction in hypothalamic glucose-receptive neurones of obese Zucker rats" Journal of Physiology 497.2:365-377 (1996).

Sarabu et al., "Glucokinase activators as new type 2 diabetes therapeutic agents" Expert Opinion on Therapeutic Patents 18(7):759-768 (2008).

Schuit et al. "Glucose sensing in pancreatic β-Cells. A model for the study of other glucose-regulated cells in gut, pancreas, and hypothalamus" Diabetes 50:1-11 (2001).

Sekera et al. "No. 69.—Recherches sur les anesthesiques locaux (XI memoire) Synthese de quelques nouveaux β-alcoxyethoxycarbanilates et β-alcoxyethoxycinchonamides amines" Soc. Chim., 5th Series, Memoires 401-404 (1959) (Translation enclosed).

Seoane et al. "Glucokinase overexpression restores glucose utilization and storage in cultured hepatocytes from male Zucker diabetic fatty rats" J Biol Chem. 274(45):31833-31838 (1999).

Shiota et al. "Glucokinase gene locus transgenic mice are resistant to the development of obesity-induced type 2 diabetes" Diabetes 50(3):622-629 (2001).

Shorvon, "Pyrrolidone derivatives" Lancet 358(9296):1885-1892 (2001).

Spanswick et al. "Insulin activates ATP-sensitive K+ channels in hypothalamic neurons of lean, but not obese rats" Nature Neuroscience 3(8):757-758 (2000).

Spanswick et al. "Leptin inhibits hypothalamic neurons by activation of ATP-sensitive potassium channels" Nature 390(6659):521-525 (1997).

Stout et al. "Synthesis and antiarrhythmic and parasympatholytic properties of substituted phenols. 3. Modifications to the linkage region (region 3)" J. Med. Chem. 28(3):295-298 (1985).

Suhua et al. "Synthesis and biological activity of tyrosine protein kinase inhibitors" Acta Pharmaceutica Sinica 32(7): 515-523 (1997).

Takagi et al. "Studies on metabolic fate of 3,4,5-trimethoxy-N-(3-piperidyl)benzamide(KU-54). (2). Metabolism in rats" Accession No. 1984:503556 HCAPLUS, Abstract of Oyo Yakuri 27(6):1167-1174 (1984).

Tecilla et al. "Hydrogen-bonding self-assembly of multichromophore structures" J. Am. Chem. Soc. 112:9408-9410 (1990).

Tecilla et al. "Synthetic hydrogen bonding receptors as models of transacylase enzymes" Tetrahedron 51(2):435-448 (1995).

Tecilla et al. "Transition-state stabilization and molecular recognition: acceleration of phosphoryl-transfer reactions by an artificial receptor" J. Am. Chem. Soc. 112:9586-9590 (1990).

Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973) (Translation enclosed).

Tucker et al. "Novel Inhibitors of prolyl 4-hydroxylase. 2. 5-amide substituted pyridine-2-carboxylic acids" J. Med. Chem. 3(5)5:804-807 (1992).

Van Gorp et al. "C3-symmetrical supramolecular architectures: fibers and organic gels from discotic trisamides and trisureas" J Am. Chem. Soc. 124(49):14759-14769 (2002).

Vanderstelt et al. "Synthesis and pharmacological properties of some derivatives of 5H-benzo[4,5]cyclohepta[1,2-b]pyridine and of 11H-benzo[5,6]cyclohepta[1,2-c]pyridine III" Arzneim. Forsch. 22(1):133-137 (1972).

Velho et al. "Impaired hepatic glycogen synthesis in glucokinase-deficient (MODY-2) subjects" J. Clin. Invest. 98(8):1755-1761 (1996).

Vertigan et al. "Impact of cell glycogen content on modulation of hepatocyte glucose metabolism by pharmacological agents" Diabetologia, 47 Supp 1, A 214, 589 (2004).

West, Anthony R., "Solid State Chemistry and its Applications" Wiley, New York, pp. 358 and 365 (1988).

Williams et al. "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) 1-4 (Oct. 2004).

Winzell et al. "Glucokinase Activation Reduces Glycemia and Improves Glucose Tolerance in Mice with High-fat Diet-induced Insulin Resistance" Abstract No. 1482-P, 67th Annual Scientific Sessions, American Diabetes Association, Chicago, IL (Jun. 22-26, 2007) and Diabetes vol. 56 (Supplement 1) 1482-P (2007).

Wolff, Manfred E. "Burger's Medicinal Chemistry", 5th Edition, Part I, John Wiley & Sons, pp. 975-977 (1995).

Yakushijin et al. "Intramolecular ring formation of phenyl azide and furan moieties" Chem. Pharm. Bull. 30(1):140-151 (1982).

Yakushijin et al. "Intramolecular ring formation of phenyl azide and furan" Heterocycles 12(8):1021-1026 (1979).

Yang et al. "Hypothalamic glucose sensor similarities to and differences from pancreatic beta-cell mechanisms" Diabetes 48(9):1763-1772 (1999).

Yoshina et al. "Studies of heterocyclic compounds.II. Synthesis of 2-furylvinyl-benzenes and studies of polarography" Yakugaku Zasshi 88(4):398-404 (1968).

Yoshina et al. "Studies of heterocyclic compounds. III. Synthesis of methyl 5-(2-phenylvinyl)2-furoate" Yakugaku Zasshi 88(4):405-409 (1968).

Yoshina et al. "Studies of heterocyclic compounds. IV. Ultraviolet spectra of 2-(2-furyl)vinylbenzenes and 2-(2-furyl)vinylfurans" Yakugaku Zasshi 88(4):410-416 (1968).

Yoshina et al. "Studies of heterocyclic compounds. VI. 2-(Carbomethoxy-2-furyl)vinyl benzenes and their ultraviolet spectra" Yakugaku Zasshi 88(4):977-983 (1968).

Youssefyeh et al. "Development of high-affinity 5-HT3 receptor antagonists. 1. Initial structure-activity relationship of novel benzamides" J. Med. Chem. 35(5): 895-903 (1992).

Zhang et al. "Synthesis based on affinity separation (SAS): separation of products having barbituric acid tag from untagged compounds by using hydrogen bond interaction" Synlett 5:590-596 (2001).

* cited by examiner

THERAPEUTIC AGENTS

This application claims the benefit under 35 U.S.C. §119(e) of Application No. 61/168,048 (US) filed on 9 Apr. 2009.

The present invention relates to (2S)-2-[1-(2-chloro-6-cyano-phenyl)pyrazolo[4,5-e]pyrimidin-4-yl]oxy-3-[(1R)-2-hydroxy-1-methyl-ethoxy]-N-(5-methylpyrazin-2-yl)propanamide which is useful in the treatment or prevention of a disease or medical condition mediated through glucokinase (GLK or GK). GK Activators (GKAs) are known to activate GK in the pancreatic β-cell leading to a decreased glucose threshold for insulin secretion. In addition GKAs activate hepatic GK thereby stimulating hepatic glucose uptake and suppressing hepatic glucose output. The net pharmacological effect of GKAs is to lower blood glucose levels. Therefore, such compounds may have utility in the treatment of Type 2 diabetes and obesity. The invention also relates to pharmaceutical compositions comprising said compounds and to methods of treatment of diseases mediated by GLK using said compounds.

The biology of glucokinase and the mechanisms by which GKAs might deliver potential therapeutic benefit in Type 2 diabetes have been extensively reviewed in the literature (see for example Matschinsky F M et al. (2006) Diabetes 55: 1-12, Leighton B, Atkinson A, Coghlan M P (2005) Biochemical Society Transactions 33: 371-374 and "Glucokinase and Glycemic Disease: From Basics to Novel Therapeutics." Frontiers in Diabetes vol 16, eds. Matschinsky F M and Magnuson M A, Karger (Basel) 2005). In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P), which is catalysed by glucokinase (GLK). GLK has a high (6-10 mM) Km for glucose and is not inhibited by physiological concentrations of G-6-P. GLK expression is limited to a few tissues and cell types, most notably pancreatic β-cells and liver cells (hepatocytes). In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes.

In one sub-type of diabetes, Maturity-Onset Diabetes of the Young Type 2 (MODY-2), the diabetes is caused by GLK loss of function mutations. Hyperglycaemia in MODY-2 patients results from defective glucose utilisation in both the pancreas and liver. Defective glucose utilisation in the pancreas of MODY-2 patients results in a raised threshold for glucose stimulated insulin secretion. Conversely, rare activating mutations of GLK reduce this threshold resulting in familial hyperinsulinism. In addition to the reduced GLK activity observed in MODY-2 diabetics, hepatic glucokinase activity is also decreased in type 2 diabetics. Importantly, global or liver selective overexpression of GLK prevents or reverses the development of the diabetic phenotype in both dietary and genetic models of the disease. Moreover, acute treatment of type 2 diabetics with fructose improves glucose tolerance through stimulation of hepatic glucose utilisation. This effect is believed to be mediated through a fructose induced increase in cytosolic GLK activity in the hepatocyte by the mechanism described below.

GLK and the $K_{ATP}$ channel are expressed in neurones of the hypothalamus, a region of the brain that is important in the regulation of energy balance and the control of food intake. These neurones have been shown to express orectic and anorectic neuropeptides and have been assumed to be the glucose-sensing neurones within the hypothalamus that are either inhibited or excited by changes in ambient glucose concentrations. The ability of these neurones to sense changes in glucose levels is defective in a variety of genetic and experimentally induced models of obesity. Intracerebroventricular (icv) infusion of glucose analogues, that are competitive inhibitors of glucokinase, stimulate food intake in lean rats. In contrast, icv infusion of glucose suppresses feeding. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK system can be described as a potential "Diabesity" target (of benefit in both Diabetes and Obesity).

GLK is also expressed in specific entero-endocrine cells where it is believed to control the glucose sensitive secretion of the incretin peptides GIP (glucose-dependent insulinotropic polypeptide) and GLP-1 (Glucagon-Like Peptide-1) from gut K-cells and L-cells respectively. Therefore, small molecule activators of GLK may have additional beneficial effects on insulin secretion, b-cell function and survival and body weight as a consequence of stimulating GIP and GLP-1 secretion from these entero-endocrine cells.

N-(Thiazolyl)-2-[(1-phenyl-1H-pyrazolo[3,4-d]pyrimidin-4-yl)thio]acetamide is disclosed in Phosphorus, Sulfur and Silicon, vol 178, 2003, pp 1795-1805 which is concerned with antimicrobial activity of related compounds. Similar compounds are also known from commercially available Chemical Libraries.

WO98/35944 discloses that compounds of formula $R^1R^2N$—C(O)—C($R^3$)($R^4$)—X—$R^5$ in which $R^1$-$R^5$ are each individually selected from a wide range of substituents and X is oxygen or sulfur are useful in treating bulimia and obesity by virtue of their activity at the NPY receptor antagonists. $R^5$ may be 1H-pyrazolo[3,4-d]pyrimidin-4-yl or 4-aminopyrazolo[3,4-d]pyrimidin-6-yl. Specific compounds exemplified are N-(4-cyclohexylphenyl)-2-(1H-pyrazolo[3,4-d]pyrimidin-4-ylsulfanyl)acetamide, N-(4-benzoylphenyl)-2-(1H-pyrazolo[3,4-d]pyrimidin-4-ylsulfanyl)acetamide, 2-(4-amino-1H-pyrazolo[3,4-d]pyrimidin-6-ylsulfanyl)-N-(4-cyclohexylphenyl)acetamide and 2-(4-amino-1H-pyrazolo[3,4-d]pyrimidin-6-ylsulfanyl)-N-(4-benzoylphenyl)acetamide.

Thus, according to the first aspect of the invention there is provided (2S)-2-[1-(2-chloro-6-cyano-phenyl)pyrazolo[4,5-e]pyrimidin-4-yl]oxy-3-[(1R)-2-hydroxy-1-methyl-ethoxy]-N-(5-methylpyrazin-2-yl)propanamide or a pharmaceutically acceptable salt thereof.

In particular the compound is (2S)-2-[1-(2-chloro-6-cyano-phenyl)pyrazolo[4,5-e]pyrimidin-4-yl]oxy-3-[(1R)-2-hydroxy-1-methyl-ethoxy]-N-(5-methylpyrazin-2-yl)propanamide.

It is to be understood that the compounds of the invention may exist in tautomeric forms and that the invention also relates to any and all tautomeric forms of the compounds of the invention which activate GLK. It will be understood that compounds described herein in their pyrimidinol form may also be described as the pyrimidinone tautomer and vice versa. This implies nothing about the actual relative proportions of the two in physical samples.

It is also to be understood that certain compounds of the invention and salts thereof can exist in solvated as well as unsolvated forms such as, for example, hydrated forms. It is to be understood that the invention encompasses all such solvated forms which activate GLK.

In a further embodiment are provided in-vivo hydrolysable esters of the compound of the invention, and in a further alternative embodiment are provided pharmaceutically-acceptable salts of in-vivo hydrolysable esters of the compound of the invention.

The compound of the invention is named as a pyrazolo[4,5-e]pyrimidin-4-yl compound. It will be understood by those skilled in the art that the compound could also be named as a pyrazolo[3,4-d]pyrimidin-4-yl compound.

The compound of the invention may be administered in the form of a pro-drug. A pro-drug is a bioprecursor or pharmaceutically acceptable compound being degradable in the body to produce a compound of the invention (such as an ester or amide of a compound of the invention, particularly an in-vivo hydrolysable ester). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen;
c) H. Bundgaard, Chapter 5 "Design and Application of Prodrugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988); and
f) N. Kakeya, et al., Chem Pharm Bull, 32, 692 (1984).

The contents of the above cited documents are incorporated herein by reference.

Examples of pro-drugs are as follows. An in-vivo hydrolysable ester of a compound of the invention containing a hydroxy group is, for example, a pharmaceutically-acceptable ester which is hydrolysed in the human or animal body to produce the parent alcohol. An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In one aspect, a suitable acid-addition salt may be one with hydrochloric, sulphuric, methanesulfonic or citric acid.

A further feature of the invention is a pharmaceutical composition comprising the compound of the invention as defined above, or a pharmaceutically-acceptable salt thereof, together with a pharmaceutically-acceptable diluent or carrier.

According to another aspect of the invention there is provided the compound of the invention or a pharmaceutically-acceptable salt thereof for use as a medicament.

According to another aspect of the invention there is provided the compound of the invention or a pharmaceutically-acceptable salt thereof as defined above for use as a medicament for treatment of a disease mediated through GLK, in particular type 2 diabetes.

Further according to the invention there is provided the use of the compound of the invention or a pharmaceutically-acceptable salt thereof in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially diabetes, by administering an effective amount of the compound of the invention or a pharmaceutically-acceptable salt thereof to a mammal in need of such treatment.

Specific diseases which may be treated by a compound or composition of the invention include: blood glucose lowering in Type 2 Diabetes Mellitus without a serious risk of hypoglycaemia (and potential to treat type 1), dyslipidemia, obesity, insulin resistance, metabolic syndrome X, impaired glucose tolerance.

As discussed above, thus the GLK system can be described as a potential "Diabesity" target (of benefit in both Diabetes and Obesity). Thus, according to another aspect of the invention there is provided the use of the compound of the invention or a pharmaceutically-acceptable salt thereof, in the preparation of a medicament for use in the combined treatment or prevention, particularly treatment, of diabetes and obesity.

According to another aspect of the invention there is provided the use of the compound of the invention or a pharmaceutically-acceptable salt thereof, in the preparation of a medicament for use in the treatment or prevention of obesity.

According to a further aspect of the invention there is provided a method for the combined treatment of obesity and diabetes by administering an effective amount of the compound of the invention or a pharmaceutically-acceptable salt thereof, to a mammal in need of such treatment.

According to another aspect of the invention there is provided a compound the compound of the invention or a pharmaceutically-acceptable salt thereof as defined above for use as a medicament for treatment or prevention, particularly treatment of obesity.

According to a further aspect of the invention there is provided a method for the treatment of obesity by administering an effective amount of the compound of the invention or a pharmaceutically-acceptable salt thereof, to a mammal in need of such treatment.

Compounds of the invention may be particularly suitable for use as pharmaceuticals, for example because of favourable physical and/or pharmacokinetic properties and/or toxicity profile.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). Dosage forms suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monoooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monoooleate, or condensation products of ethylene oxide with partial esters derived from fatty acids and hexitol anhydrides, for example polyethylene sorbitan monoooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monoooleate) and condensation products of the said partial esters with ethylene oxide such as polyoxyethylene sorbitan monoooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the compound of the invention will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The elevation of GLK activity described herein may be applied as a sole therapy or in combination with one or more other substances and/or treatments for the indication being treated. In another aspect the invention provides a pharmaceutical combination comprising a compound of the invention and another pharmacologically active substance particularly wherein the other pharmacologically active substance is a medicament for the treatment of type 2 diabetes or obesity or a related condition.

Such conjoint treatment may be achieved by way of the simultaneous, sequential or separate administration of the individual components of the treatment. Simultaneous treatment may be in a single tablet or in separate tablets. For example in the treatment of diabetes mellitus, chemotherapy may include the following main categories of treatment:

1) Insulin and insulin analogues;
2) Insulin secretagogues including sulphonylureas (for example glibenclamide, glipizide), prandial glucose regulators (for example repaglinide, nateglinide);
3) Agents that improve incretin action (for example dipeptidyl peptidase IV inhibitors e.g. saxagliptin, sitagliptin, vildagliptin or alogliptin and GLP-1 agonists);
4) Insulin sensitising agents including PPARgamma agonists (for example pioglitazone and rosiglitazone), and agents with combined PPARalpha and gamma activity;
5) Agents that modulate hepatic glucose balance (for example metformin, fructose 1, 6 bisphosphatase inhibitors, glycogen phosphorylase inhibitors, glycogen synthase kinase inhibitors);
6) Agents designed to reduce the absorption of glucose from the intestine (for example acarbose);
7) Agents that prevent the reabsorption of glucose by the kidney (SGLT inhibitors for example dapagliflozin);
8) Agents designed to treat the complications of prolonged hyperglycaemia (for example aldose reductase inhibitors);
9) Anti-obesity agents (for example sibutramine and orlistat);
10) Anti-dyslipidaemia agents such as, HMG-CoA reductase inhibitors (eg statins); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
11) Antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
12) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin;
13) Agents which antagonise the actions of glucagon; and
14) Anti-inflammatory agents, such as non-steroidal anti-inflammatory drugs (eg. aspirin) and steroidal anti-inflammatory agents (eg. cortisone).

The compound of the invention, or a salt thereof, may be prepared by any process known to be applicable to the preparation of such compounds or structurally related compounds. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991.

Processes for the synthesis of the compound of the invention are provided as a further feature of the invention. Thus, according to a further aspect of the invention there is provided a process for the preparation of a compound of the invention as described in the examples.

In a further aspect the present invention provides a process for the preparation of (2S)-2-[1-(2-chloro-6-cyano-phenyl)pyrazolo[4,5-e]pyrimidin-4-yl]oxy-3-[(1R)-2-hydroxy-1-methyl-ethoxy]-N-(5-methylpyrazin-2-yl)propanamide comprising de-protecting a compound of formula A

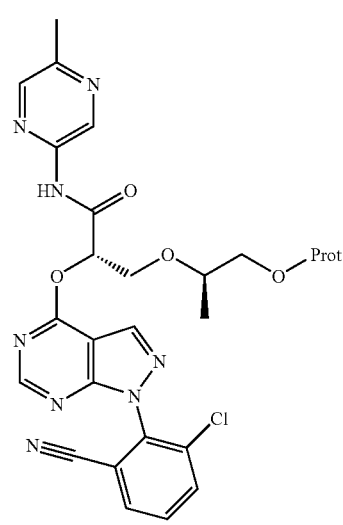

in which Prot represents a hydroxy protecting group.

Examples of hydroxy protecting groups include methyl, t-butyl, lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); tetrahydropyran-2-yl; aryl lower alkyl groups (e.g. benzyl) groups; and triaryl lower alkyl groups (e.g. triphenylmethyl).

Methods appropriate for removal of hydroxy protecting groups include, for example, nucleophilic displacement, acid-, base-, metal- or enzymically-catalysed hydrolysis, catalytic hydrogenolysis/hydrogenation or photolytically for groups such as o-nitrobenzyloxycarbonyl. Silyl groups may be removed with fluoride ions for example using tetrabutylammonium fluoride in a solvent, for example an ether e.g. tetrahydrofuran or an alkanoic acid for example acetic acid, at a temperature from 0° C. to the boiling point of the solvent or more particularly in the range 5° C.-35° C. Silyl groups may be also removed with a mineral acid for example hydrochloric acid, particularly dilute hydrochloric acid, at a temperature from 0° C. to 50° C., particularly 15-30° C. Silyl groups may be removed with organic acids e.g alkylsulfonic acids, for example methanesulfonic acid, or arylsulfonic acids, for example benzenesulfonic acid. Methylether protecting groups for hydroxy groups may be removed by trimethylsilyliodide. A tert-butyl ether protecting group for a hydroxy group may be removed by treatment with an acid, for example by use of hydrochloric acid in methanol.

Certain intermediates used to prepare the compound of the invention are believed to be novel and are herein claimed as a further embodiment of the present invention. In another aspect the present invention provides a compound of formula A. Particularly Prot represents a tri lower alkyl/arylsilyl groups (e.g. trimethylsilyl, t-butyldimethylsilyl, t-butyldiphenylsilyl).

In a further embodiment the present invention provides one or more of the following:
(2S)-2-(1-(2-chloro-6-cyanophenyl)-1H-pyrazolo[3,4-d]pyrimidin-4-yloxy)-N-(5-methylpyrazin-2-yl)-3-((R)-1-(triisopropylsilyloxy)propan-2-yloxy)propanamide;
(S)-2-hydroxy-N-(5-methylpyrazin-2-yl)-3-((R)-1-(triisopropylsilyloxy)propan-2-yloxy)propanamide; and
(2S)-2-[1-(2-bromo-6-chlorophenyl)pyrazolo[4,5-e]pyrimidin-4-yl]oxy-N-(5-methylpyrazin-2-yl)-3-[(2R)-1-tri(propan-2-yl)silyloxypropan-2-yl]oxypropanamide.

The following examples are for illustration purposes and are not intended to limit the scope of this application. Each exemplified compound represents a particular and independent aspect of the invention. In the following non-limiting Examples, unless otherwise stated:

(i) evaporations were carried out by rotary evaporation under reduced pressure and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Examples were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; quin, quintet; sextet (v) intermediates were not generally fully characterised and purity was assessed by thin layer chromatography (TLC), high-performance liquid chromatography (HPLC), infra-red (IR) or NMR analysis;

(vi) flash chromatography was carried out on silica unless otherwise stated;

(vii) Enantiomeric excesses (ee's) were determined by HPLC using a chiral stationary phase such as Chiralcel OJ or Chiralpak AD-H and/or by NMR using an appropriate chiral shift reagent such as (1S)-[1,1'-binaphthalene]-2,2'-diol (CAS 18531-99-2) or (1R)-[1,1'-binaphthalene]-2,2'-diol (CAS 18531-94-7).

ABBREVIATIONS

ACN Acetonitrile
n-BuLi n-Butyllithium
m-CPBA 3-Chloroperbenzoic acid
DCM Dichloromethane
DIPEA Di-iso-propylethylamine
DMAP 4-Di(methylamino)pyridine
DMF N,N-Dimethylformamide
DMSO dimethylsulfoxide
EtOAc Ethyl acetate
EtOH Ethanol
FMOC 9-Fluorenylmethyl carbamate
IPA Isopropyl alcohol
LHMDS Lithium bis(trimethylsilyl)amide
MeOH Methanol
TBDMSCl tert-Butyldimethylsilyl chloride
THF Tetrahydrofuran
ESI Electrospray ionisation
rt Room temperature
cat Catalytic
ee Enantiomeric excess
HPLC High performance liquid chromatography
EDCI 1-(3-Dimethylaminopropyl)-2-ethylcarbodiimide hydrochloride
rel vols relative volumes
equiv molar equivalents

EXAMPLE 1

(2S)-2-[1-(2-chloro-6-cyano-phenyl)pyrazolo[4,5-e]pyrimidin-4-yl]oxy-3-[(1R)-2-hydroxy-1-methylethoxy]-N-(5-methylpyrazin-2-yl)propanamide

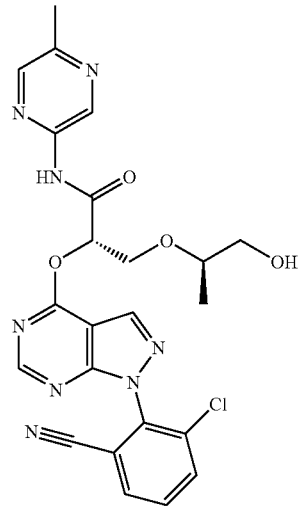

A solution of tetrabutylammonium fluoride (1M in THF) (0.887 mL, 0.89 mmol) was added in one portion to a stirred solution of (2S)-2-(1-(2-chloro-6-cyanophenyl)-1H-pyrazolo[3,4-d]pyrimidin-4-yloxy)-N-(5-methylpyrazin-2-yl)-3-((R)-1-(triisopropylsilyloxy)propan-2-yloxy)propanamide (Intermediate AZ1) (0.59 g, 0.89 mmol) in tetrahydrofuran (15 mL). The resulting solution was stirred at ambient temperature for 30 minutes. The reaction mixture was quenched with saturated NH$_4$Cl (10 mL), and diluted with water (20 mL) and EtOAc (70 mL). The organic layer was separated and the aqueous layer extracted with EtOAc (70 mL), The combined organics were dried (MgSO$_4$), filtered and evaporated to afford crude product. The crude product was purified by flash silica chromatography, elution gradient 50 to 80% EtOAc in isohexane to afford the product (0.367 g, 81%). $^1$H NMR (400 MHz, CDCl3) δ 1.14-1.20 (3H, m), 2.54 (3H, s), 2.70-2.84 (1H, m), 3.54-3.72 (2H, m), 3.77-3.83 (1H, m), 4.09-4.16 (1H, m), 4.28-4.32 (1H, m), 6.08-6.11 (1H, m), 7.63 (1H, t), 7.78-7.81 (1H, m), 7.85-7.88 (1H, m), 8.12 (1H, s), 8.50-8.53 (1H, m), 8.62 (1H, d), 9.04-9.12 (1H, m), 9.41 (1H, s); m/z (ES$^+$) (M+H)$^+$=509.06; HPLC t$_R$=2.41 min.

(2S)-2-(1-(2-chloro-6-cyanophenyl)-1H-pyrazolo[3,4-d]pyrimidin-4-yloxy)-3-((R)-1-hydroxypropan-2-yloxy)-N-(5-methylpyrazin-2-yl)propanamide (220 mg, 0.43 mmol) was taken up into Et$_2$O (20 mL) and warmed to boiling under reflux. The material dissolved and then began to crystallise. The mixture was allowed to cool and stood at ambient temperature for 1 hour. The solid was filtered off to give (2S)-2-(1-(2-chloro-6-cyanophenyl)-1H-pyrazolo[3,4-d]pyrimidin-4-yloxy)-3-((R)-1-hydroxypropan-2-yloxy)-N-(5-methylpyrazin-2-yl)propanamide (200 mg) which was shown to be crystalline by x-ray powder diffraction.

| Angle 2-Theta (2θ) | Intensity % |
| --- | --- |
| 4.234 | 100.0 |
| 20.902 | 95.6 |
| 14.456 | 95.2 |
| 17.730 | 77.8 |
| 13.278 | 69.4 |
| 11.065 | 63.2 |
| 21.237 | 61.5 |
| 19.725 | 59.4 |
| 26.458 | 59.2 |
| 8.463 | 54.9 |
| 26.192 | 54.8 |

EXAMPLE 1

(2S)-2-[1-(2-chloro-6-cyano-phenyl)pyrazolo[4,5-e]pyrimidin-4-yl]oxy-3-[(1R)-2-hydroxy-1-methylethoxy]-N-(5-methylpyrazin-2-yl)propanamide
Alternative method

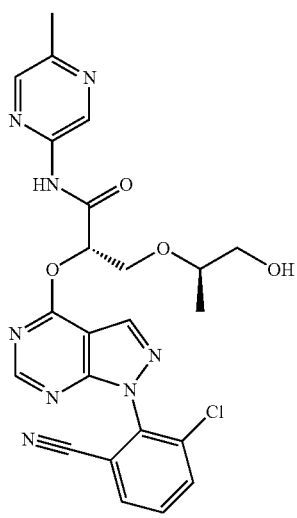

Tetrabutylammonium fluoride 1M in THF (5.11 mL, 5.11 mmol) was added to (2S)-2-(1-(2-chloro-6-cyanophenyl)-1H-pyrazolo[3,4-d]pyrimidin-4-yloxy)-N-(5-methylpyrazin-2-yl)-3-((R)-1-(triisopropylsilyloxy)propan-2-yloxy)propanamide (Intermediate AZ1) (3.4 g, 5.11 mmol) and acetic acid (0.307 g, 5.11 mmol) in THF (35 mL). The resulting solution was stirred at 22° C. for 20 hours. It was quenched with NH$_4$Cl solution (sat., 25 mL) and diluted with EtOAc (50 mL). The organic phase was washed with saturated sodium bicarbonate (25 mL), water (20 mL), brine (20 mL), dried (MgSO$_4$) and evaporated. 6 The crude product was purified by flash silica chromatography, eluting with EtOAc to afford the product (2.23 g, 85%). This was crystallised from EtOAc (10 mL) and iso-hexane (6 mL) to give the desired product as a white crystalline powder (1.9 g, 73%) confirmed to be of the same crystalline form as that described previously.

$^1$H NMR (400 MHz, DMSO-d$_6$) δ 1.06-1.07 (3H, m), 2.44 (3H, s), 3.25-3.47 (2H, m), 3.62-3.67 (1H, m), 4.09-4.16 (2H, m), 4.53-4.61 (1H, m), 5.90-5.96 (1H, m), 7.89 (1H, dd), 8.16-8.20 (2H, m), 8.31-8.32 (1H, m), 8.62 (1H, s), 8.76-8.78 (1H, m), 9.10-9.12 (1H, m), 11.17 (1H, s); m/z (ES$^-$) (M−H)$^-$=507; HPLC t$_R$=2.44 min.

EXAMPLE 1

(2S)-2-[1-(2-chloro-6-cyano-phenyl)pyrazolo[4,5-e]pyrimidin-4-yl]oxy-3-[(1R)-2-hydroxy-1-methylethoxy]-N-(5-methylpyrazin-2-yl)propanamide
Alternative method

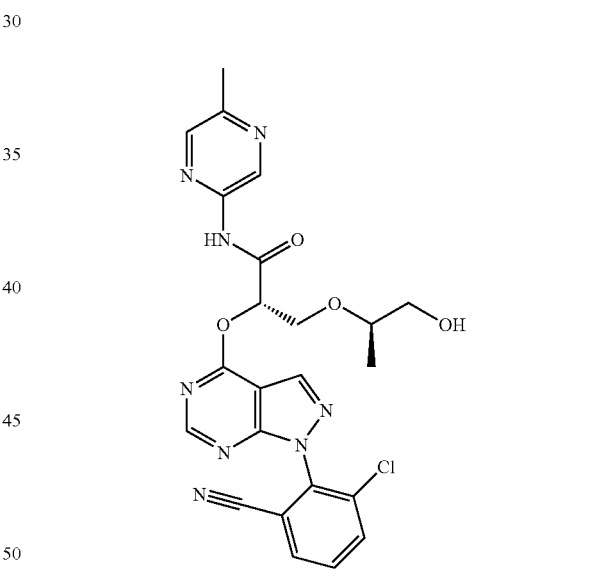

Hydrochloric acid (6M, 4 equivs) was added with stirring to a solution of (2S)-2-(1-(2-chloro-6-cyanophenyl)-1H-pyrazolo[3,4-d]pyrimidin-4-yloxy)-N-(5-methylpyrazin-2-yl)-3-((R)-1-(triisopropylsilyloxy)propan-2-yloxy)propanamide (Intermediate AZ1) (1 equiv) in propan-2-ol (9 rel vols) in an inert atmosphere at ambient temperature. The mixture was stirred for 6 hours then basified carefully with aqueous sodium bicarbonate solution. The volume was reduced to half of the original volume by distillation under reduced pressure and then ethyl acetate and water were added. The mixture was stirred and then the phases were separated. The aqueous phase was extracted with ethyl acetate and the combined organic extract and washings were dried by azeotropic distillation. The product was crystallised from a mixture of ethyl acetate/heptane (5:6 vols). Yield 84%.

PREPARATION OF INTERMEDIATES

Intermediate AH1: di-tert-butyl 1-(2-bromo-6-chlorophenyl)hydrazine-1,2-dicarboxylate

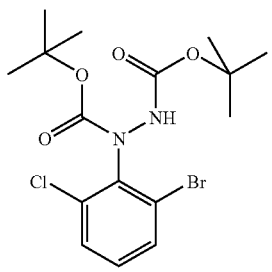

To a stirred solution of 2.5 M Butyllithium in hexanes (13.79 mL, 34.47 mmol) at −20° C. was added dropwise 2,2,6,6-tetramethylpiperidine (5.82 mL, 34.47 mmol) in THF (30 mL). This was stirred for 30 minutes. This solution was cooled down to −78° C., and a solution of 1-bromo-3-chlorobenzene (6 g, 31.34 mmol) in THF (20 mL) was added dropwise so as to maintain the temperature at <−70° C. After 2 hours (Z)-di-tert-butyl diazene-1,2-dicarboxylate (10.82 g, 47.01 mmol) in THF (30 mL) added dropwise at −78° C. Stirred at this temperature for 2 hours, then allowed to warm to room temperature overnight. Water (150 mL) added. The mixture was extracted with EtOAc (2×300 mL). The extracts were combined, washed with brine (100 mL), dried (MgSO$_4$) and reduced go give a residue which was purified by flash silica chromatography, elution gradient 0-10% EtOAc in hexane. Fractions containing suspected product were combined, and reduced to give di-tert-butyl 1-(2-bromo-6-chlorophenyl)hydrazine-1,2-dicarboxylate (9.59 g, 72.5%) $^1$H NMR (400 MHz, DMSO) δ 1.30-1.50 (18H, s), 7.28 (1H, m), 7.55 (1H, dd), 7.67 (1H, dd), 9.18 (1H, s). m/z (ES+) (M+Na)$^+$=443; HPLC t$_R$=10.76 min.

Intermediate AH2: (2-bromo-6-chlorophenyl)hydrazine hydrochloride

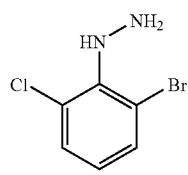

4M Hydrogen chloride in dioxane (28.2 mL, 112.64 mmol) was added to di-tert-butyl 1-(2-bromo-6-chlorophenyl)hydrazine-1,2-dicarboxylate (Intermediate AH1) (9.5 g, 22.53 mmol) in iPrOH (30 mL) at ambient temperature. The resulting solution was heated to 60° C. and stirred for 20 minutes. The reaction mixture was allowed to cool to ambient temperature. A solid was filtered off, and dried under vacuum to afford the product (4.71 g). $^1$H NMR (400 MHz, DMSO) d 6.97 (1H, s), 7.06 (1H, t), 7.41 (1H, dd), 7.52 (1H, dd), 9.83 (3H, s). m/z M$^+$=220; GC-MS tR=10.419 min.

Intermediate AH3: 5-amino-1-(2-bromo-6-chlorophenyl)-1H-pyrazole-4-carbonitrile

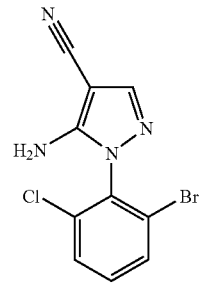

(2-Bromo-6-chlorophenyl)hydrazine hydrochloride (Intermediate AH2) (4.71 g, 18.26 mmol) was partitioned between DCM (300 mL) and 2M NaOH (20 mL). Allowed to Stir for 1 hour. The two phases were separated. The organic phase was reduced under vacuum to give the free base. This was dissolved in MeOH (60 mL), and stirred in a cooling bath at 0° C. (Ethoxymethylene)malononitrile (2.230 g, 18.26 mmol) added portionwise. The reaction mixture was then allowed to warm to ambient temperature and stirred for 1 hour. The mixture was then heated to reflux and stirred for 16 hours. Allowed to cool to ambient temperature. The reaction mixture was concentrated to give a solid, which was triturated under MeOH. A solid was filtered off. This was dried to afford the product (4.59 g, 85%). $^1$H NMR (400 MHz, DMSO) δ 6.79 (2H, s), 7.54-7.47 (1H, m), 7.70 (1H, dd), 7.79 (1H, s), 7.81 (1H, d). m/z (ES+) (M+H)$^+$=299; HPLC t$_R$=1.70 min.

Intermediate AH4: 1-(2-bromo-6-chlorophenyl)-1H-pyrazolo[3,4-d]pyrimidin-4(5H)-one

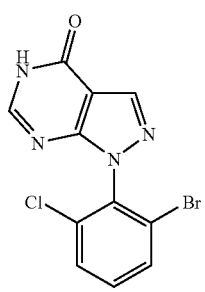

Concentrated sulfuric acid (0.905 mL, 16.97 mmol) was added to a stirred solution of 5-amino-1-(2-bromo-6-chlorophenyl)-1H-pyrazole-4-carbonitrile (Intermediate AH3) (4.59 g, 15.43 mmol) in formic acid (30 mL). The resulting solution was heated to 100° C. and stirred for 4 hours. The reaction mixture was allowed to cool to ambient temperature. The reaction mixture was evaporated to dryness. The residue was triturated under water. A solid was filtered off. This was dried under vacuum to afford the product (3.71 g, 73.8%). $^1$H NMR (400 MHz, DMSO) δ 7.58 (1H, t), 7.80-7.76 (1H, m), 7.88 (1H, dd), 8.08 (1H, d), 8.40 (1H, s), 12.44 (1H, s). m/z (ES+) (M+H)$^+$=327; HPLC t$_R$=1.48 min.

Intermediate AH5: 3-chloro-2-(4-hydroxy-1H-pyrazolo[3,4-d]pyrimidin-1-yl)benzonitrile

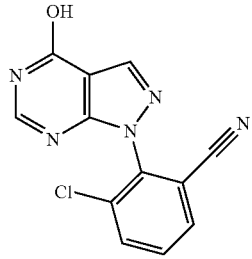

1-(2-bromo-6-chlorophenyl)-1H-pyrazolo[3,4-d]pyrimidin-4(5H)-one (Intermediate AH4) (1012 mg, 3.11 mmol) and zinc cyanide (329 mg, 2.80 mmol) were dissolved in DMF (15 mL). Sealed into a microwave tube. The tube was purged with nitrogen. 9,9-Dimethyl-4,5-bis(diphenylphosphino)xanthene (180 mg, 0.31 mmol) and tris(dibenzylideneacetone)dipalladium(0) (142 mg, 0.16 mmol) added. The reaction was heated to 160° C. for 15 minutes in the microwave reactor, then allowed to cool to ambient temperature. The DMF was removed by evaporation. The crude product was absorbed onto silica and then purified by flash silica chromatography, elution gradient 0 to 10% MeOH in DCM to afford the product (769 mg, 91%). $^1$H NMR (400 MHz, DMSO) δ 7.89-7.83 (1H, t), 8.14 (1H, s), 8.15 (2H, d), 8.49 (1H, s), 12.56 (1H, s); m/z (ES+) (M+H)$^+$=272; HPLC $t_R$=1.29 min.

Intermediate AH6: 3-Chloro-2-(4-chloro-1H-pyrazolo[3,4-d]pyrimidin-1-yl)benzonitrile

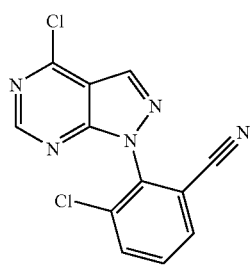

Phosphorus oxychloride (7.93 mL, 85.03 mmol) was added to 3-chloro-2-(4-hydroxy-1H-pyrazolo[3,4-d]pyrimidin-1-yl)benzonitrile (Intermediate AH5) (1.155 g, 4.25 mmol). The resulting mixture was heated to 100° C. and stirred for 4 hours. The reaction mixture was allowed to cool to ambient temperature. The reaction mixture was evaporated to near dryness. Poured onto ice/water with stirring. A solid precipitate was collected by filtration. This was dried overnight under vacuum to afford the product (0.928 g, 75%). $^1$H NMR (400 MHz, DMSO) δ 8.02-7.96 (1H, t), 8.26 (1H, d), 8.28 (1H, s), 9.05 (2H, d). m/z M$^+$=289; GCMS tR=13.82 min.

Intermediate AN1: (S)-Methyl 3-((R)-1-(tert-butyldimethylsilyloxy)propan-2-yloxy)-2-hydroxypropanoate

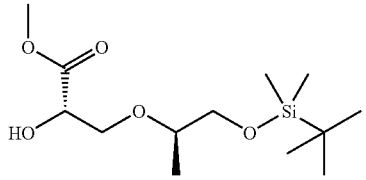

Magnesium trifluoromethanesulfonate (1.165 g, 3.61 mmol) was added in one portion to (S)-methyl oxirane-2-carboxylate (1.475 g, 14.45 mmol) and (R)-1-(tert-butyldimethylsilyloxy)propan-2-ol (CAS no. 136918-07-5) (2.75 g, 14.45 mmol) cooled to 10° C. The resulting suspension was stirred at 10° C. for 10 minutes and then warmed to 45° C. and stirred for 2 days. The crude product was purified by flash silica chromatography, eluting with 0 to 30% EtOAc in isohexane to afford the product (1.680 g, 39.8%). $^1$H NMR (400 MHz, DMSO) δ 0.00 (s, 6H), 0.83 (s, 9H), 0.98 (d, 3H), 3.35-3.45 (m, 2H), 3.47-3.65 (m, 3H), 3.66 (s, 3H), 4.09-4.15 (m, 1H), 5.37 (d, 1H).

Intermediate AU5: (S)-methyl 2-hydroxy-3-((R)-1-(triisopropylsilyloxy)propan-2-yloxy)propanoate

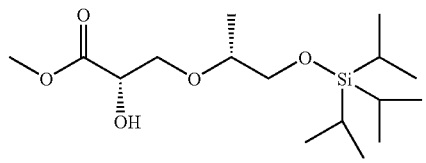

Prepared using a procedure analogous to that described for Intermediate AN1 using (R)-1-(triisopropylsilyloxy)propan-2-ol (CAS no. 871657-72-6). $^1$H NMR (400 MHz, CDCl$_3$) δ 1.04-1.16 (24H, m), 3.39 (1H, d), 3.54-3.59 (2H, m), 3.67-3.72 (1H, m), 3.78 (3H, s), 3.80-3.91 (2H, m), 4.27-4.31 (1H, m).

Intermediate AU5: (R)-methyl 2-hydroxy-3-((S)-1-(triisopropylsilyloxy)propan-2-yloxy)propanoate
Alternative Procedure Magnesium trifluoromethanesulfonate (1.263 g, 3.92 mmol) was added to a mixture of (S)-1-(triisopropylsilyloxy)propan-2-ol (4.55 g, 19.59 mmol) and (R)-methyl oxirane-2-carboxylate (2 g, 19.59 mmol) in ethyl acetate (40 mL). The resulting suspension was heated to 80° C. for 72 hours. Further (R)-methyl oxirane-2-carboxylate (2 g, 19.59 mmol) was added and the mixture stirred at 80° C. for 48 hrs. Further (R)-methyl oxirane-2-carboxylate (2 g, 19.59 mmol) was added and the mixture stirred for 24 hrs. The mixture was allowed to cool, filtered through a bed of silica (~10 g), washed through with EtOAc and evaporated. The crude product was purified by flash silica chromatography, elution gradient 10 to 50% EtOAc in isohexane, to afford the product (2.7 g, 41%).

Intermediate AZ1: (2S)-2-(1-(2-chloro-6-cyanophenyl)-1H-pyrazolo[3,4-d]pyrimidin-4-yloxy)-N-(5-methylpyrazin-2-yl)-3-((R)-1-(triisopropylsilyloxy)propan-2-yloxy)propanamide Intermediate AZ1: (2S)-2-[1-(2-chloro-6-cyanophenyl)pyrazolo[4,5-e]pyrimidin-4-yl]oxy-N-(5-methylpyrazin-2-yl)-3-[(2R)-1-tri(propan-2-yl)silyloxypropan-2-yl]oxypropanamide. Alternative preparation

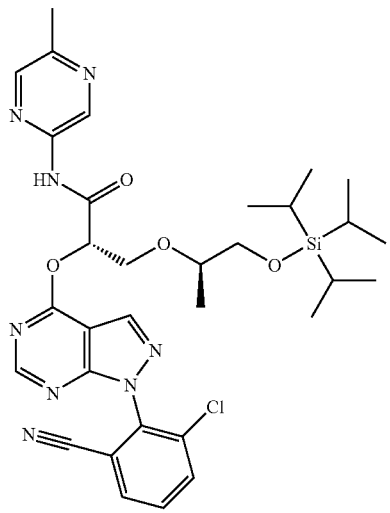

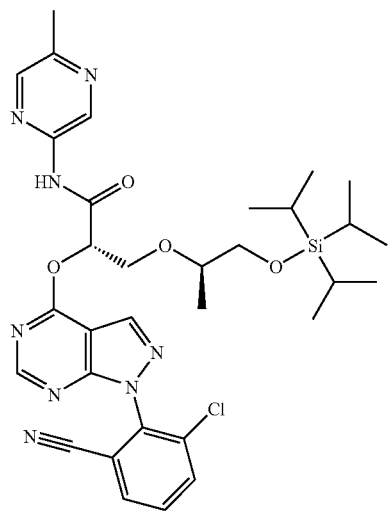

Sodium hydride (60% dispersion in mineral oil) (0.116 g, 2.89 mmol) was added to (S)-2-hydroxy-N-(5-methylpyrazin-2-yl)-3-((R)-1-(triisopropylsilyloxy)propan-2-yloxy)propanamide (Intermediate AZ2) (0.595 g, 1.45 mmol) in anhydrous THF (20 mL) at 0° C. under nitrogen. The resulting solution was stirred at 0° C. for 10 minutes and then 3-chloro-2-(4-chloro-1H-pyrazolo[3,4-d]pyrimidin-1-yl)benzonitrile (Intermediate AH6) (0.438 g, 1.31 mmol) was added. The reaction mixture was allowed to warm to room temperature and stirred for 1 hour. The reaction mixture was adjusted to pH 7 by addition of 1M citric acid and the majority of the THF removed in vacuo. The reaction mixture was diluted with water (20 mL) and EtOAc (50 mL). The organic layer was separated and the aqueous layer re-extracted with EtOAc (2×100 mL). The combined organics were washed with saturated brine (75 mL), dried (MgSO$_4$) and evaporated. The crude product was purified by flash silica chromatography, eluting with 50 to 100% EtOAc in isohexane to afford the product (0.590 g, 67.5%). $^1$H NMR (400 MHz, CDCl$_3$) δ 0.98-1.08 (21H, m), 1.12-1.17 (3H, m), 2.54 (3H, s), 3.59-3.78 (3H, m), 4.21-4.26 (1H, m), 4.29-4.36 (1H, m), 6.02-6.06 (1H, m), 7.60-7.65 (1H, m), 7.78-7.81 (1H, m), 7.85-7.87 (1H, m), 8.11-8.13 (1H, m), 8.50 (1H, d), 8.61 (1H, d), 8.71 (1H, d), 9.44 (1H, t); m/z (ES$^+$) M$^+$=665.26; HPLC $t_R$=4.02 min.

Tris(dibenzylideneacetone)dipalladium(0) (0.261 g, 0.29 mmol) was added in one portion to a de-gassed mixture of (2S)-2-(1-(2-bromo-6-chlorophenyl)-1H-pyrazolo[3,4-d]pyrimidin-4-yloxy)-N-(5-methylpyrazin-2-yl)-3-((2R)-1-(triisopropylsilyloxy)propan-2-yloxy)propanamide (Intermediate BO1) (4.1 g, 5.70 mmol), zinc cyanide (0.335 g, 2.85 mmol) and 9,9-dimethyl-4,5-bis(diphenylphosphino)xanthene (0.330 g, 0.57 mmol) in N-methylpyrrolidone (41 mL) at 20° C. under nitrogen. The resulting suspension was degassed under vacuum with inlet of nitrogen four times and then heated to 110° C. (internal temperature) for 1 hour. The mixture was cooled, poured into water (100 mL) and extracted with ethyl acetate (2×50 mL). The organic layers were combined and washed with water (4×50 mL) and brine (50 mL), dried over MgSO$_4$, filtered and evaporated. The crude product was purified by flash silica chromatography, elution gradient 30 to 100% EtOAc in isohexane to afford the product (3.0 g, 79%). $^1$H NMR (400.13 MHz, DMSO-d$_6$) δ 0.90-1.08 (21H, m), 1.09-1.11 (3H, m), 2.45 (3H, s), 3.53-3.58 (1H, m), 3.60-3.66 (1H, m), 3.75-3.78 (1H, m), 4.10-4.15 (2H, m), 5.94-5.99 (1H, m), 7.87-7.91 (1H, m), 8.16-8.19 (2H, m), 8.31-8.33 (1H, m), 8.60-8.61 (1H, m), 8.73 (1H, s), 9.10-9.12 (1H, d), 11.20 (1H, s); m/z (ES$^-$) (M–H)$^-$=663; HPLC $t_R$=3.79 min.

Intermediate AZ1: (2S)-2-[1-(2-chloro-6-cyanophenyl)pyrazolo[4,5-e]pyrimidin-4-yl]oxy-N-(5-methylpyrazin-2-yl)-3-[(2R)-1-tri(propan-2-yl)silyloxypropan-2-yl]oxypropanamide. Alternative preparation

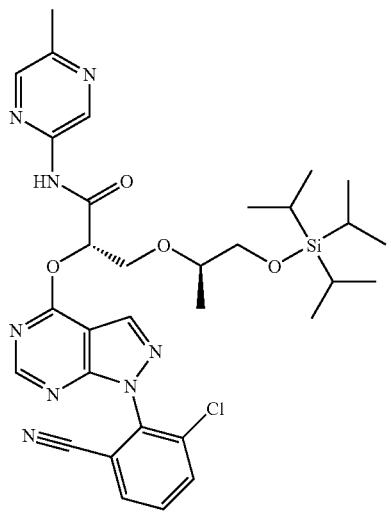

A solution of (2S)-2-(1-(2-bromo-6-chlorophenyl)-1H-pyrazolo[3,4-d]pyrimidin-4-yloxy)-N-(5-methylpyrazin-2-yl)-3-((R)-1-(triisopropylsilyloxy)propan-2-yloxy)propanamide (Intermediate BO1) (1 equiv) in inerted* DMF (5 rel vols) and diisopropylethylamine (DIPEA) (1.25 equivs) was kept in an inert atmosphere and was added with stirring to an inerted* mixture of tris(dibenzylideneacetone)dipalladium (0) (0.025 equivs), sodium acetate (0.1 equiv) and 1,1'-bis(diphenylphosphino)ferrocene (0.075 equivs) in DMF (5 rel vols) at 90° C. over 5 minutes. The mixture was stirred for 10 minutes and then an inerted* solution of acetone cyanohydrin (1.4 equivs) in DMF (2 rel vols) was added over 20 hours with stirring. When the reaction was completed the mixture was cooled to 5° C. and diluted with methyl tert-butyl ether (7 rel vols) and then sodium bicarbonate (0.3 equivs) in water (2.5 rel vols). The organic phase was separated and the aqueous phase washed with methyl tert-butyl ether. The combined organic extract and organic washings were evaporated under reduced pressure at 35° C. and the residue was purified by chromatography. Yield 74%. *Nitrogen bubbled through before use.

Intermediate AZ2: (S)-2-hydroxy-N-(5-methylpyrazin-2-yl)-3-((R)-1-(triisopropylsilyloxy)propan-2-yloxy)propanamide

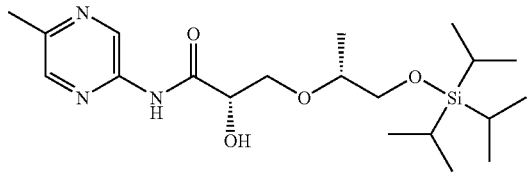

Trimethylaluminium (2M solution in toluene) (5.98 mL, 11.96 mmol) was added to 5-methylpyrazin-2-amine (1.305 g, 11.96 mmol) in toluene (20 mL) cooled to 0° C. under nitrogen. The resulting solution was stirred at 0° C. for 20 minutes. (R)-methyl 2-hydroxy-3-((S)-1-(triisopropylsilyloxy)propan-2-yloxy)propanoate (Intermediate AU5) (2 g, 5.98 mmol) in toluene (6 mL) was added and the reaction was allowed to warm to room temperature and then refluxed for 6 hours. The reaction mixture was allowed to cool and concentrated in vacuo. The residue was neutralised with citric acid (1M, aq.) and then diluted with water (25 mL) and extracted with EtOAc (2×50 mL). The combined organics were washed with brine (20 mL), then dried (MgSO$_4$) and evaporated. The crude product was purified by flash silica chromatography, eluting with 30 to 50% EtOAc in isohexane to afford the product (1.390 g, 56.5%). $^1$H NMR (400 MHz, CDCl$_3$) δ 1.04-1.17 (24H, m), 2.54 (3H, s), 3.62-3.67 (3H, m), 3.81-3.85 (1H, m), 4.05-4.09 (1H, m), 4.22 (1H, d), 4.34 (1H, q), 8.13 (1H, d), 9.12 (1H, s), 9.44 (1H, d); m/z (ES$^+$) (M+H)$^+$= 412.34; HPLC t$_R$=3.82 min.

Intermediate AZ2: (S)-2-hydroxy-N-(5-methylpyrazin-2-yl)-3-((R)-1-(triisopropylsilyloxy)propan-2-yloxy)propanamide. Alternative preparation Trimethylaluminium (2M solution in toluene) (72.5 mL, 145 mmol) was added to 5-methylpyrazin-2-amine (13.64 g, 125.0 mmol) in toluene (520 mL) cooled to 0° C. under nitrogen. The resulting solution was stirred at 0° C. for 20 minutes. (R)-methyl 2-hydroxy-3-((S)-1-(triisopropylsilyloxy)propan-2-yloxy)propanoate (Intermediate AU5) (33.5 g, 100.0 mmol) in toluene (130 mL) was added and the reaction was allowed to warm to room temperature and then stirred at 72° C. for 2.5 hours. The reaction mixture was allowed to cool then poured into a stirred mixture of ethyl acetate (500 mL) and aqueous solution of Rochelle salt (20% w/v, 500 mL). The mixture was stirred for 15 minutes then the organics separated and washed with water (500 mL) followed by brine (500 mL), then dried (MgSO$_4$), filtered and concentrated. The residues were dissolved in iso-hexane (300 mL) and stood for 15 minutes at 20° C. before cooling to 5° C. over 30 minutes. The solid formed was isolated by filtration, washed with iso-hexane cooled to 5° C. (200 mL) and dried at 40° C. under high vacuum to afford the product (26.7 g, 64%). The filtrates were combined and concentrated to 100 mL total volume and the mixture stood for 16 hours. The solid formed was isolated by filtration, washed with iso-hexane cooled to 5° C. (100 mL), dried at 40° C. under high vacuum and combined with the initial batch to afford the product (30.1 g, 73%). $^1$H NMR (400 MHz, CDCl$_3$) δ 1.04-1.17 (24H, m), 2.54 (3H, s), 3.62-3.67 (3H, m), 3.81-3.85 (1H, m), 4.05-4.09 (1H, m), 4.22 (1H, d), 4.34 (1H, q), 8.13 (1H, d), 9.12 (1H, s), 9.44 (1H, d); m/z (ES$^+$) (M+H)$^+$=412.34; HPLC t$_R$=3.82 min.

Intermediate BO1: (2S)-2-[1-(2-bromo-6-chlorophenyl)pyrazolo[4,5-e]pyrimidin-4-yl]oxy-N-(5-methylpyrazin-2-yl)-3-[(2R)-1-tri(propan-2-yl)silyloxypropan-2-yl]oxypropanamide

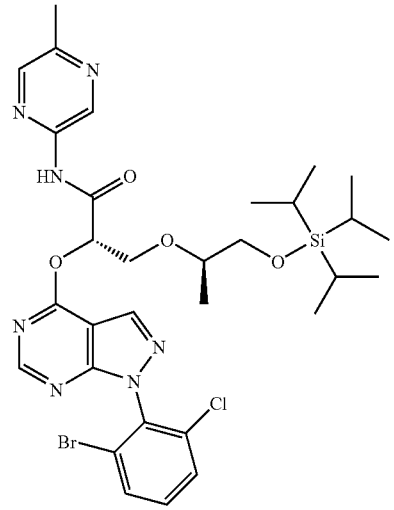

Sodium hydride (0.875 g, 21.87 mmol) was added to (S)-2-hydroxy-N-(5-methylpyrazin-2-yl)-3-((R)-1-(triisopropylsilyloxy)propan-2-yloxy)propanamide (Intermediate AZ2) (3.0 g, 7.29 mmol) in anhydrous THF (35 mL) at 0° C. under nitrogen. The resulting solution was stirred at 0° C. for 10 minutes and then a solution of 1-(2-bromo-6-chlorophenyl)-4-chloro-1H-pyrazolo[3,4-d]pyrimidine (Intermediate BO2) (2.507 g, 7.29 mmol) in anhydrous THF (20 mL) was added dropwise over 1 minute. The mixture was stirred at 0° C. for 10 minutes and then allowed to warm to ambient temperature for 6 hours. It was then cooled to ~0° C., the mixture poured into ice cold 1M citric acid and diluted with EtOAc (50 mL). It was stirred vigorously for 10 minutes. The organic phase was separated, washed with water and brine, dried over MgSO$_4$, filtered and evaporated. The crude product was purified by flash silica chromatography, elution gradient 20 to 50% EtOAc in isohexane to afford the product (4.90 g, 93%).

$^1$H NMR (400.13 MHz, DMSO-d$_6$) δ 0.88-1.03 (21H, m), 1.09-1.11 (3H, m), 2.44 (3H, s), 3.52-3.57 (1H, m), 3.63-3.67 (1H, m), 3.73-3.78 (1H, m), 4.09-4.18 (2H, m), 5.92-5.98 (1H, m), 7.60-7.64 (1H, m), 7.80-7.83 (1H, m), 7.91-7.93 (1H, m), 8.30-8.31 (1H, m), 8.53-8.54 (1H, m), 8.63 (1H, s), 9.11 (1H, s), 11.19 (1H, s); m/z (ES$^-$) (M−H)$^-$=718; HPLC t$_R$=3.95 min.

Intermediate BO1: (2S)-2-[1-(2-bromo-6-chlorophenyl)pyrazolo[4,5-e]pyrimidin-4-yl]oxy-N-(5-methylpyrazin-2-yl)-3-[(2R)-1-tri(propan-2-yl)silyloxypropan-2-yl]oxypropanamide. Alternative method

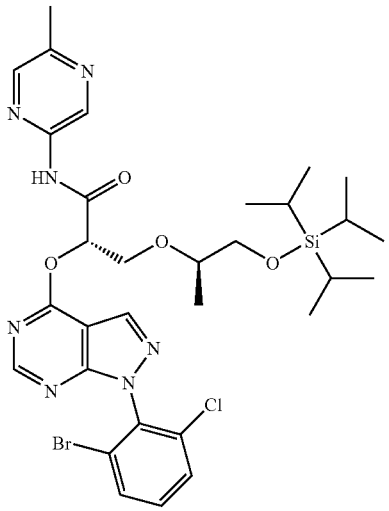

A solution of 1-(2-bromo-6-chlorophenyl)-4-chloro-1H-pyrazolo[3,4-d]pyrimidine (Intermediate BO2) (1.03 equivs) in toluene (8 rel vols) and THF (2 rel vols) was added to a stiffed mixture containing an aqueous sodium hydroxide solution (4 equivs) and (S)-2-hydroxy-N-(5-methylpyrazin-2-yl)-3-(R)-1-(triisopropylsilyloxy)propan-2-yloxy)propanamide (Intermediate AZ2) (1.00 equiv) in toluene (2 rel vols) and THF (5 rel vols) at 10° C. The mixture was allowed to warm to ambient temperature and stirred at ambient temperature until full conversion (1 hour). The reaction mixture was added to a cold mixture of citric acid (3 equivs), water (4.5 rel vols) and toluene (8 rel vols) with stiffing. The mixture was allowed to warm up to ambient temperature with stirring. The mixture was separated and the organic phase was washed with brine and concentrated. The product is obtained by evaporation of the solvent. Yield 94%.

Intermediate BO2: 1-(2-bromo-6-chlorophenyl)-4-chloropyrazolo[4,5-e]pyrimidine

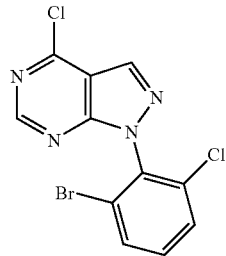

Phosphoryl trichloride (30.4 ml, 326.37 mmol) was added in one portion to 1-(2-bromo-6-chlorophenyl)-1H-pyrazolo[3,4-d]pyrimidin-4-ol (Intermediate AH4) (4.25 g, 13.05 mmol) and the resulting suspension was stirred at 100° C. for 2 hours.

It was then cooled and evaporated. The residue was dissolved in toluene (60 mL), poured onto ice, diluted with ethyl acetate (40 mL) and stirred for 1 hour. The organic phase was separated, washed with water (4×25 mL) and brine (25 mL), dried over MgSO$_4$, filtered and evaporated to a pale yellow oil that crystallised on standing to afford the product (4.3 g, 95%) which was used without further purification.

$^1$H NMR (400.13 MHz, DMSO-d$_6$) δ 7.66 (1H, dd), 7.84 (1H, dd), 7.94 (1H, dd), 8.89 (1H, s), 8.93 (1H, s); m/z (ES$^+$) (M+H)$^+$=345; HPLC t$_R$=2.90 min.

Intermediate BO2: 1-(2-bromo-6-chlorophenyl)-4-chloropyrazolo[4,5-e]pyrimidine. Alternative procedure

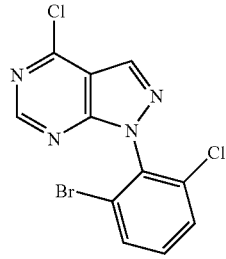

Phosphoryl trichloride (4 equivs) was added to a slurry of 1-(2-bromo-6-chlorophenyl)-1H-pyrazolo[3,4-d]pyrimidin-4-ol (Intermediate AH4) (1 equiv) in acetonitrile (3 rel vols) with stirring under nitrogen followed by diisopropylethylamine (4 equivs). The reaction mixture was boiled under reflux with stirring for 15 hours. The mixture was cooled to ambient temperature and toluene (12 rel vols) was added. The mixture was cooled at 1° C. and quenched with water (3 rel vols) keeping the temperature below 20° C. The organic layer was separated off and washed with water, then with aqueous sodium bicarbonate solution then dried to give a solution of the product in toluene. Yield 94%.

Biological Tests:

The biological effects of the compound of the invention may be tested in the following way:

(1) Enzymatic Activity

Enzymatic activity of recombinant human pancreatic GLK may be measured by incubating GLK, ATP and glucose. The rate of product formation may be determined by coupling the assay to a G-6-P dehydrogenase, NADP/NADPH system and measuring the linear increase with time of optical density at 340 nm as described in Brocklehurst et al (Diabetes 2004, 53, 535-541).

The compound of the invention has been found to have the following mean $EC_{50}$ (μM):

| Ex. No. | EC50/uM |
|---------|---------|
| 1 | 0.4415 |

Production of Recombinant GLK:

Human GLK was obtained by PCR from human pancreatic mRNA respectively, using established techniques described in Sambrook J, Fritsch E F & Maniatis T, 1989. PCR primers were designed according to the GLK cDNA sequences shown in Tanizawa et al 1991 and Bonthron, D. T. et al 1994 (later corrected in Warner, J. P. 1995).

Cloning in Bluescript II Vectors

GLK was cloned in E. coli using pBluescript II, (Short et al 1998) a recombinant cloning vector system similar to that employed by Yanisch-Perron C et al (1985), comprising a colEI-based replicon bearing a polylinker DNA fragment containing multiple unique restriction sites, flanked by bacteriophage T3 and T7 promoter sequences; a filamentous phage origin of replication and an ampicillin drug resistance marker gene.

Transformations

E. Coli transformations were generally carried out by electroporation. 400 mL cultures of strains DH5a or BL21(DE3) were grown in L-broth to an OD 600 of 0.5 and harvested by centrifugation at 2,000 g. The cells were washed twice in ice-cold deionised water, resuspended in 1 mL 10% glycerol and stored in aliquots at −70° C. Ligation mixes were desalted using Millipore V Series™ membranes (0.0025 mm) pore size). 40 mL of cells were incubated with 1 mL of ligation mix or plasmid DNA on ice for 10 minutes in 0.2 cm electroporation cuvettes, and then pulsed using a Gene Pulser™ apparatus (BioRad) at 0.5 kVcm$^{-1}$, 250 mF. Transformants were selected on L-agar supplemented with tetracyline at 10 mg/mL or ampicillin at 100 mg/mL.

Expression

GLK was expressed from the vector pTB375NBSE in E. coli BL21 cells, producing a recombinant protein containing a 6-His tag immediately adjacent to the N-terminal methionine. Alternatively, another suitable vector is pET21(+)DNA, Novagen, Cat number 697703. The 6-His tag was used to allow purification of the recombinant protein on a column packed with nickel-nitrilotriacetic acid agarose purchased from Qiagen (cat no 30250).

(2) Oral Glucose Tolerance Test (OGTT) or Glucose Profile

Oral glucose tolerance tests were done on conscious Zucker obese fa/fa rats (age 12-13 weeks or older). The animals were fasted for 2 hours before use for experiments. A test compound or a vehicle was given orally 120 minutes before oral administration of a glucose solution at a dose of 2 g/kg body weight. Blood glucose levels were measured using a Accucheck glucometer from tail bled samples taken at different time points before and after administration of glucose (time course of 60 minutes). A time curve of the blood glucose levels was generated and the area-under-the-curve (AUC) for 120 minutes was calculated (the time of glucose administration being time zero). Percent reduction in glucose excursion was determined using the AUC in the vehicle-control group as zero percent reduction.

For Glucose profile a test compound or vehicle was given 60 minutes before conscious Zucker obese fa/fa rats (age 12-13 weeks or older) entered a dark cycle (12-hours). Blood glucose mevels were measured using a Accucheck glucometer from tail bled samples taken at different time points during the 12-hour dark cycle. A time curve of the blood glucose levels was generated and the area-under-the-curve (AUC) for 12-hours was calculated (the beginning of the dark cycle being time zero). Percent reduction in glucose excursion was determined using the AUC in the vehicle-control group as zero percent reduction.

The invention claimed is:

1. (2S)-2-[1-(2-Chloro-6-cyano-phenyl)pyrazolo[4,5-e]pyrimidin-4-yl]oxy-3-[(1R)-2-hydroxy-1-methyl-ethoxy]-N-(5-methylpyrazin-2-yl)propanamide or a pharmaceutically acceptable salt thereof.

2. The compound as claimed in claim 1 which is (2S)-2-[1-(2-chloro-6-cyano-phenyl)pyrazolo[4,5-e]pyrimidin-4-yl]oxy-3-[(1R)-2-hydroxy-1-methyl-ethoxy]-N-(5-methylpyrazin-2-yl)propanamide.

3. The compound as claimed in either claim 1 or claim 2 in crystalline form.

4. A pharmaceutical composition comprising a compound as claimed in either claim 1 or claim 2 together with a pharmaceutically acceptable diluent or carrier.

5. A process for the preparation of (2S)-2-[1-(2-chloro-6-cyanophenyl)pyrazolo[4,5-e]pyrimidin-4-yl]oxy-3-[(1R)-2-hydroxy-1-methyl-ethoxy]-N-(5-methylpyrazin-2-yl)propanamide comprising de-protecting a compound of formula A

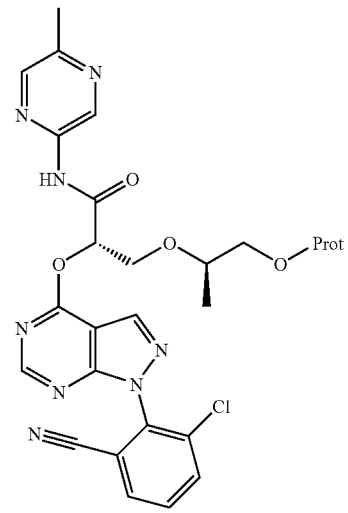

in which Prot represents a hydroxy protecting group.

* * * * *